United States Patent [19]

Papp

[11] 4,064,246

[45] Dec. 20, 1977

[54] HYDROXYMETHYL-SUBSTITUTED-2(1H)-QUINAZOLINONES

[75] Inventor: Eugene A. Papp, Parsippany, N.J.

[73] Assignee: Sandoz, Inc., E. Hanover, N.J.

[21] Appl. No.: 731,336

[22] Filed: Oct. 12, 1976

[51] Int. Cl.² .................. C07D 239/82; A61K 31/505
[52] U.S. Cl. .............................. 424/251; 260/251 QB
[58] Field of Search .................. 260/251 QB; 424/251

[56] References Cited

U.S. PATENT DOCUMENTS 3,723,432   3/1973   Ott .................................. 260/251 QB 3,812,118   5/1974   Yamamoto et al. .............. 260/247.1

FOREIGN PATENT DOCUMENTS 1,181,570   2/1970   France.

*Primary Examiner*—Raymond V. Rush
*Attorney, Agent, or Firm*—Gerald D. Sharkin; Richard E. Vila; Frederick H. Weinfeldt

[57] ABSTRACT

Hydroxymethyl-substituted-2(1H)-quinazolinones, e.g., 7-hydroxymethyl-1-isopropyl-4-phenyl-2(1H)-quinazolinone, are useful as anti-inflammatory agents.

16 Claims, No Drawings

HYDROXYMETHYL-SUBSTITUTED-2(1H)-QUINAZOLINONES

This invention relates to quinazolinone compounds and more particularly to hydroxymethyl-substituted-2(1H)-quinazolinone compounds, to pharmaceutical compositions containing such compounds and to the pharmaceutical use of such compounds; as well as to novel intermediates.

The quinazolinone compounds of this invention may conveniently be represented by the formula I:

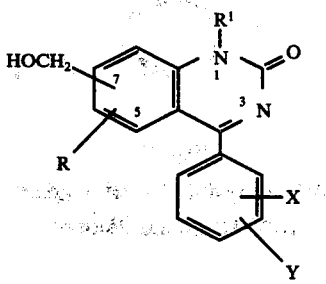

wherein $R^1$ is alkyl having from 1 to 6 carbon atoms, or cycloalkylalkyl (unsubstituted) of from 4 to 8 carbon atoms; in which the cycloalkyl portion is a ring of from 3 to 6 carbon atoms, and the alkyl portion has one or 2 carbon atoms, i.e. it is a methylene or ethylene radical;

R is a hydrogen atom or halo having an atomic weight of from about 18 to 36, i.e., fluoro or chloro;

X is a hydrogen atom, halo having an atomic weight of from about 18 to 80, i.e., fluoro, chloro or bromo, alkoxy having from 1 to 4 carbon atoms, e.g., methoxy, or hydroxy; and Y is a hydrogen atom, halo having an atomic weight of from about 18 to 36, or alkoxy having from 1 to 4 carbon atoms.

Generally preferred compounds of the invention have any one or more of the following features: (a) $R^1$ being branched alkyl; (b) R being hydrogen; (c) X being hydrogen or fluoro; and (d) Y being hydrogen. Within the above-indicated general preferences are the following more desired preferences: (a) $R^1$ being isopropyl, (b) the hydroxymethyl substituent being at the 7-position; and (c) X being hydrogen or p-fluoro. The particularly preferred compounds have two or more of the above-indicated general preferences and desired preferences in combination, and the especially preferred compounds have all such general preferences in combination and the still further especially preferred compounds have all the desired preferences in combination.

Compounds I are obtainable by basic hydrolysis (process a) of their corresponding mono-bromo analogs, i.e., compounds II:

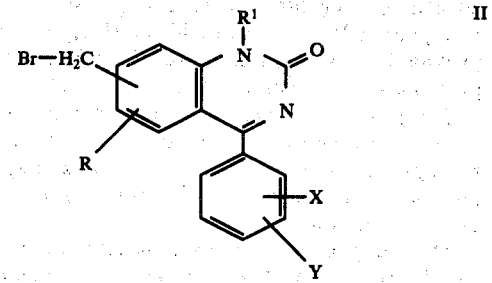

wherein R, $R^1$, X and Y are as defined above.

The basic hydrolysis of a compound II (process a) may be suitably carried out in a basic aqueous medium at temperatures of from about 40° C to 120° C, and at a pH of from about 8 to 11, employing a water-soluble alkali-metal salt of a weak acid such as sodium carbonate or sodium acetate to provide the basic conditions. The reaction medium preferably includes up to about 67% (by volume) of an inert water-miscible cosolvent, such as lower alkanol, e.g., methanol; preferably about 10 to 50% (by volume). Preferred reaction temperatures are from about 60° to 100° C. It is particularly convenient to carry out the hydrolysis at the reflux temperature of the reaction mixture. Particular attention should be given to the selection of the alkali metal salt, and the pH of the reaction mixture in order to obtain optimum yields as the aryl-hydroxymethyl structure may be decomposed to a certain extent under basic reaction conditions.

The compounds of the formula II may be produced by mono-bromination (process b) of a compound of the formula III:

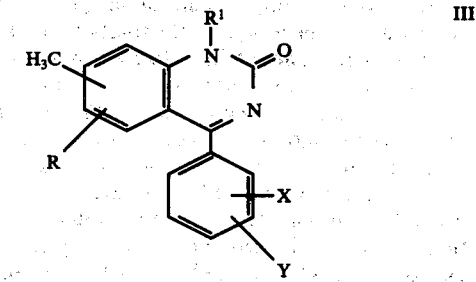

wherein, R, $R^1$, X and Y are as defined above.

The bromination (process b) may be effected in accordance with known procedures for brominating an aromatic methyl substituent. The reaction is typically carried out at temperatures in the range of from about 40° to 150° C, preferably from about 50° to 100° C., and desirably under the influence of infra red light. The reaction is carried out in an inert organic solvent, such as carbon tetrachloride. The preferred brominating agent is N-bromosuccinimide.

Where a compound I in which X is hydroxy is desired it is preferred to employ a Compound III bearing a hydroxy function in protected form, e.g. as an alkanoyloxy function of 2 to 5 carbon atoms, preferably an acetoxy function, which is retained during process (b) but hydrolizes during process (a) to yield a corresponding Compound I in which X is —OH. Suitable protected compounds are obtainable by acylating a Compound III in which X = —OH in conventional manner for acylating a phenolic —OH function. The compounds of the formula II in which X also represents an alkanoyloxy function of 2 to 5 carbon atoms, ie. Compounds II'; represent additional novel compounds provided by the invention. In such Compounds II'; X is preferably other than hydroxy.

The products of the above-described reactions may be recovered and refined in conventional manner, e.g., by crystallization, distillation or chromatographic techniques, such as eluting from a chromatographic column or separating on a silica layer.

The compounds of the formula III are either known, e.g., from U.S. Pat. No. 3,723,432, or may be produced in accordance with the known procedures from known materials.

The compounds of structural formula I are useful because they possess pharmacological activity in animals. In particular, the compounds are useful as anti-inflammatory agents as indicated by the Carrageenan-induced edema test on rats (oral and i.v. administration), wherein: (a) the difference in foot volume is measured by difference in mercury displacement (the drug effect being measured 3 hours after carrageenan); and (b) the swelling of the paw edema and drug effect are measured by an Antiphlogmeter according to Hemper and Ameln, Zeitschr. Ges. Exp. Med. 131, 407(1959), by determining the change in capacity in a condenser (the drug effect being the average of readings taken 3 and 5 hours after carrageenan).

For such use, the compounds may be combined with a pharmaceutically acceptable carrier, and such other conventional adjuvants as may be necessary; and administered orally in such forms as tablets, capsules, dispersible powders, granules, suspensions containing, for example, from about 0.5% to 5% of suspending agent, syrups containing, for example, from about 10% to 50% of sugar, and elixirs containing, for example from about 20% to 50% of ethanol, and the like, or perenterally in the form of sterile injectable solutions or suspensions containing from about 0.5% to 5% suspending agent in an isotonic medium. These pharmaceutical preparations may contain, for example, from 0.5% up to about 90% of the active ingredient in combination with the carrier, more usually between 5% and 60% by weight. The dosage administered will, of course, vary depending upon the compounds used and the mode of administration. However, in general, satisfactory results are obtained when administered at a daily dosage of from about 3.0 milligrams to about 200 milligrams per kilogram of body weight, preferably orally and in divided doses 2 to 4 times a day, or in sustained release form. For most mammals, the administration of from about 200 milligrams to about 2000 milligrams of the compound per day provides satisfactory results and dosage forms suitable for internal administration comprise from about 50 milligrams to about 1000 milligrams of the compound in admixture with a solid or liquid pharmaceutical carrier.

The compounds I of the invention are also useful as analgesics as indicated by application of pressure to yeast-inflamed foot of the rat (oral administration). For such use, the compounds may be administered to obtain satisfactory results at dosages and in modes similar to those employed in the treatment of inflammation.

The following examples show representative compounds encompassed within the scope of this invention and the manner in which such compounds are prepared. However, it is to be understood that the example is for purposes of illustration only. Temperatures are in Centigrade; room temperature being from about 20° to 30° C. Mixed eluants are given in volume: volume ratios.

Preparation 1

4-(3-Acetoxyphenyl)-1-isopropyl-7-methyl-2(1H)-quinazolinone

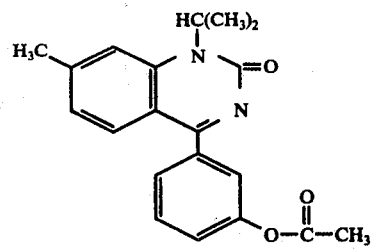

Step A, 3,4-Dihydro-1-isopropyl-4-(3-methoxyphenyl)-7-methyl-2(1H)-quinazolinone

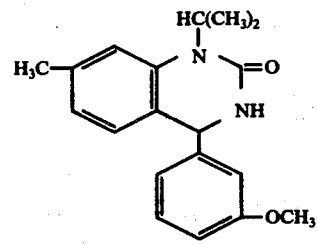

To a vessel equipped with agitation means, thermometer and a reflux condenser is added 6.40 g of N-isopropyl, N-(m-tolyl) urea, 22.21 g of m-methoxy benzaldehyde, and 255 ml of toluene. The temperature of the mixture is slowly raised (about 25 min.) to 110° C to start refluxing. After refluxing for 5 min. the temperature is lowered to 100° C and 0.12 g (0.082 ml) of methanesulphonic acid is added. The temperature is again increased to 110° C and refluxing maintained for 3 hours. The reaction mixture is then allowed to cool to room temperature, washed 4 times with dilute sulfuric acid (20% w/v) resulting in the formation of a brown-orange gummy material (undesirable material). The organic phase is then washed 4 times with 25 ml portion of water (pH of last wash 5), then dried over anh. sodium sulfate and evaporated (steam distilled) to obtain a residue. The residue is taken up in benzene, and chromatographed on a silica column; starting with benzene then increasing proportions of chloroform (20%, 50%, then 100% chloroform). The samples obtained from 100% chloroform are combined, evaporated to dryness, then crystallized from chloroform to obtain 3,4-dihydro-1-isopropyl-4-(3-methoxyphenyl)-7-methyl-2(1H)-quinazolinone, mp 167°-169°.

Step B,
1-Isopropyl-4-(3-methoxyphenyl)-7-methyl-2(1H)-quinazolinone

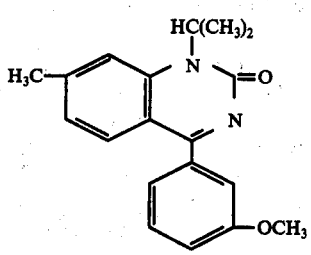

1.555 g of 3,4-dihydro-1-isopropyl-4-(3-methoxyphenyl)-7-methyl-2(1H)-quinazolinone in 40 ml of p-dioxane is charged to a vessel having a dropping funnel, agitation means and thermometer. The charged vessel is cooled in a water bath (running water at 14°); a solution of 0.88 g of potassium permanganate in 20 ml of water is placed in the dropping funnel, which is then added dropwise to the vessel with stirring during which temperatures range from 15° to 18° C). The reaction mixture is then allowed to rise to room temperature (26°), at which it is stirred for 2 hr. 20 min.; 0.38 ml of aqueous formaldehyde (37%) is then added, and the mixture stirred for 10 minutes. The mixture is then filtered through celite (diatomaceous earth), and the filtrate retained. The filter cake is then washed with 75 ml of water/p-dioxane (20:15), the washings and filtrate are combined, extracted four times with 20 ml portions methylenechloride. The combined extracts are then evaporated to dryness to obtain a residue which is taken up in 100 ml benzene, 100 ml of petroleum ether added thereto, the solution filtered through 0.5 g of charcoal, (at room temperature) and then evaporated to dryness to obtain 1-isopropyl-4-(3-methoxyphenyl)-7-methyl-2(1H)-quinazolinone.

Step C,
1-Isopropyl-4-(3-hydroxyphenyl)-7-methyl-2(1H)-quinazolinone.

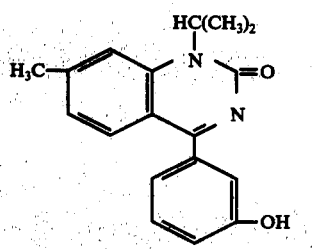

To 0.5 g of 1-isopropyl-4-(3-methoxyphenyl)-7-methyl-2(1H)-quinazolinone is added 5 ml of 48% (aqueous) hydrobromic acid (heat evolves and the solution turns yellow). The mixture is then refluxed for 6 hours. The mixture is cooled to room temperature, then 95 ml of water added, and the resulting mixture extracted thrice with 100 ml portions of a benzene: n-butanol (8:2) mixture each extract is retained separately). Each extract is washed 4 times with 75 ml portions of water (the pH of the last wash should be neutral). The extracts are combined and evaporated to dryness to obtain a residue which is then crystallized from methanol and ethyl acetate (1:1) to obtain 1-isopropyl-4-(3-hydroxyphenyl)-7-methyl-2(1H)-quinazolinone; m.p. 270°-272°, which yields refined product upon recrystallization from methanol; m.p. 274°-275° C.

Step D,
4-(3-acetoxyphenyl)-1-isopropyl-7-methyl-2(1H) quinazolinone

To 5.0 g of refined 1-isopropyl-4-(3-hydroxyphenyl)-7-methyl-2(1H)-quinazolinone in a vessel, is added 100 ml. of acetic anhydride and 0.5 ml of concentrated sulfuric acid. The resulting mixture is allowed to stand for 16 hours. The reaction mixture is then poured over salted ice in a vessel. After the ice has melted, the resulting liquid is extracted twice with 300 ml portions of benzene: n-butanol (4:1) and the combined extracts washed with distilled water until free of acid, and then evaporated to obtain a residue. The residue is crystallized from methanol to obtain the title product, m.p. 148°-150°.

EXAMPLE 1
7-Hydroxymethyl-4-(3-hydroxyphenyl)-1-isopropyl-2(1H)-quinazolinone

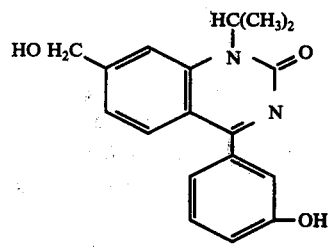

Step A,
4-(3-acetoxyphenyl)-7-bromomethyl-1-isopropyl-2(1H)-quinazolinone

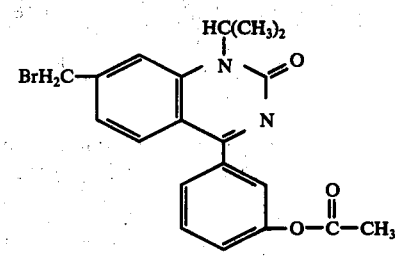

A mixture of 14 g of 4-(3-acetoxyphenyl)-1-isopropyl-7-methyl-2(1H)-quinazolinone, 20 g of N-bromosuccinimide, and 600 ml of carbon tetrachloride is irradiated with infrared light for 15 minutes in a 1000 ml flat-bottom flask while stirring and refluxing. After cooling to room temperature with an ice bath, the mixture is washed successively with 500 ml and 100 ml of water in a 2 liter separatory funnel. Each water phase is washed with an additional 100 ml of carbon tetrachloride. The combined carbon tetrachloride phase is evaporated to dryness. The resulting residue is dissolved in 200 ml of methanol and evaporated to dryness to obtain crude 4-(3-acetoxyphenyl)-7-bromomethyl-1-isopropyl-2(1H)-quinazolinone. A thin-layer chromatogram on Silica Gel GE with ethyl acetate as the mobile phase shows the presence of the desired monobrominated product and dibrominated by-product.

Step B, 7-hydroxymethyl-4-(3-hydroxyphenyl)-1-isopropyl-2(1H)-quinazolinone

The crude 4-(3-acetoxyphenyl)-7-bromomethyl-1-isopropyl-2(1H)-quinazoline residue obtained in Step A, above, is taken up in 600 ml of methanol, 200 ml of water, and 40 g of sodium acetate and refluxed for 7 hours. The reaction mixture is then diluted with 2 liters of water and extracted 3 times with 500 ml portions of ethyl acetate. The ethyl acetate phases are washed 4 times with 100 ml portions of water, combined, and evaporated to dryness. The residue is taken up in chloroform and as a slurry, placed onto a chromatography column containing 800 g of silica gel in chloroform. The column is eluted with 3 liters of ethyl acetate-chloroform (1:3), 10 liters of ethyl acetate-chloroform (1:1), and 10 liters of ethyl acetate. During the elution, 500 ml fractions are collected and analyzed by thin-layer chromatography on Silica Gel GF plates with ethyl acetate as the mobile phase. The fractions containing the title product are combined and evaporated to dryness to obtain crude title produce as a residue. The residue is dissolved in methanol, treated with charcoal in cold solution, and crystallized from hot methanol to obtain refined title product, m.p. 234°-236°.

EXAMPLE 2

7-hydroxymethyl-1-isopropyl-4-phenyl-2(1H)-quinazolinone

Step A: Preparation of 7-bromomethyl-1-isopropyl-4-phenyl-2(1H)-quinazolinone.

A mixture of 5.56 g of 1-isopropyl-7-methyl-4-phenyl-2(1L H)-quinazolinone, 7.00 g of N-bromosuccinimide and 300 ml of carbon tetrachloride is refluxed for 5 minutes in a round-bottomed flask wrapped with aluminum foil and illuminated during the refluxing with a 250 Watt I.R. lamp. The resulting mixture is then rapidly cooled to room temperature and extracted 2 times each with 300 ml of distilled water. The organic extracts are combined, filtered through glass wool and evaporated to dryness to obtain crude 7-bromomethyl-1-isopropyl-4-phenyl-2(1H)-quinazolinone (contaminated with starting material and 7-dibromomethyl-1-isopropyl-4-phenyl-2(1H)-quinazolinone by product).

Step B: Preparation of 7-hydroxymethyl-1-isopropyl-4-phenyl-2(1H)-quinazolinone.

A mixture of 69.3 of crude 7-bromomethyl-1-isopropyl-4-phenyl-2(1H)-quinazolinone (obtained by repeating Step A, above), 500 ml of a 10% aqueous sodium carbonate solution and 500 ml of methanol is refluxed for 8 hours, cooled, diluted by addition of 200 ml of distilled water containing 6 ml of 10N sodium hydroxide solution, and the resulting mixture extracted 3 times each with 400 ml of chloroform. Each extract is then washed twice with 200 ml portions of distilled water. The organic extracts are combined and evaporated to dryness to obtain a residue. The residue, thus obtained, is taken up in 100 ml of a mixture of chloroform: benzene (1:1), which solution is then placed on a chromatographic column of 480 g of silica gel in the same solvent. The column is eluted and fractions of from about 600 to 750 ml taken, in turn with 3 liters of chloroform: benzene (1:1) (fractions 1 to 4); 2 liters of 100% chloroform (fractions 5 to 7); 5 liters of ethyl acetate: chloroform (1:3) (fractions 8 to 14); and lastly 3 liters of ethyl acetate: Chloroform (1:1) (fractions 15 to 18). Fractions 9 to 14 are combined and evaporated to dryness to obtain a residue which yields refined title compound on repeated crystallization from ethyl acetate, m.p. 223°-225°.

Repeating the procedure of Step A of this Example, but replacing the 1-isopropyl-7-methyl-4-phenyl-2(1H)-quinazolinone used therein with an approximately equivalent amount of:

a) 4-(4-fluorophenyl)-1-isopropyl-7-methyl-2(1H)-quinazolinone b) 4-(3-methoxyphenyl)-1-isopropyl-7-methyl-2(1H)-quinazolinone; or c) 4-(4-chlorophenyl)-1-isopropyl-7-methyl-2(1H)-quinazolinone;

there is accordingly obtained:

a) 4-(4-fluorophenyl)-7-hydroxymethyl-1-isopropyl-2(1H)-quinazolinone;

b) 4-(3-methoxyphenyl)-7-hydroxymethyl-1-isopropyl-2(1H)-quinazolinone; and c) 4-(4-chlorophenyl)-7-hydroxymethyl-1-isopropyl 2(1H)-quinazolinone.

EXAMPLE 3

Representative formulations are tablets and capsules prepared by conventional techniques for administration 2 to 4 times a day for treatment of inflammation and containing the following ingredients:

| Ingredient | Weight (in mg) | |
|---|---|---|
| | Tablet | Capsule |
| 7-hydroxymethyl-1-isopropyl-4-phenyl-2(1H)-quinazolinone | 100 | 100 |
| Tragacanth | 10 | — |
| Lactose | 147.5 | 150 |
| Corn Starch | 25 | — |
| Talcum | 15 | — |
| Magnesium Stearate | 2.5 | — |
| TOTAL | 300 | 250 |

What is claimed is:

1. A compound of the formula

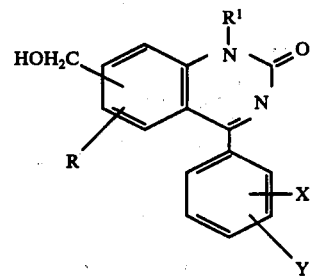

wherein $R^1$ is alkyl having from 1 to 6 carbon atoms or cycloalkylalkyl of from 4 to 8 carbon atoms in which the cycloalkyl portion has from 3 to 6 carbon atoms and the alkyl portion has 1 or 2 carbon atoms;

R is a hydrogen atom, fluoro or chloro;

X is a hydrogen atom, fluoro, chloro, bromo, alkoxy having from 1 to 4 carbon atoms, or hydroxy; and Y is a hydrogen atom, fluoro, chloro or alkoxy having from 1 to 4 carbon atoms.

2. A compound of claim 1 in which R is a hydrogen atom.

3. A compound of claim 1 in which $R^1$ is isopropyl.

4. A compound of claim 1 in which Y is a hydrogen atom.

5. A compound of claim 4 in which X is a hydrogen atom.

6. A compound of claim 4 in which X is a parafluoro.

7. A compound of claim 1 in which the hydroxymethyl function is at the 7-position.

8. A compound of claim 2 in which Y is a hydrogen atom.

9. A compound of claim 8 in which X is a hydrogen atom.

10. The compound of claim 9 which is 7-hydroxymethyl-1-isopropyl-4-phenyl-2(1H)-quinazolinone.

11. A compound of claim 8 in which X is metahydroxy.

12. The compound of claim 11 which is 7-hydroxymethyl-4-(3-hydroxyphenyl)-1-isopropyl-2(1H) quinazolinone.

13. A composition in unit dose form which is useful in treating inflammation comprising a compound of claim 1 and a pharmaceutically acceptable carrier.

14. A method of treating inflammation in a mammal in need of such treatment, comprising administering to said mammal an amount of a compound of claim 1 effective in treating said inflammation.

15. The method of claim 14 in which $R^1$ is isopropyl.

16. The method of claim 15 in which the compound is 7-hydroxymethyl-1-isopropyl-4-phenyl-2(1H)-quinazolinone.

* * * * *